(12) United States Patent
Lee et al.

(10) Patent No.: US 8,986,611 B2
(45) Date of Patent: Mar. 24, 2015

(54) SAMPLE ANALYSIS APPARATUS

(75) Inventors: Yong Koo Lee, Yongin-Si (KR); Tae Soo Kim, Yongin-si (KR); In Duk Hwang, Inchun (KR); Seock Woo Jang, Suwon-si (KR); Chul Ho Yun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 316 days.

(21) Appl. No.: 13/565,240

(22) Filed: Aug. 2, 2012

(65) Prior Publication Data

US 2013/0033708 A1   Feb. 7, 2013

(30) Foreign Application Priority Data

Aug. 2, 2011   (KR) .................. 10-2011-0077046

(51) Int. Cl.
*G01N 15/06* (2006.01)
*G01N 35/00* (2006.01)
*G01N 1/44* (2006.01)
*G01N 35/04* (2006.01)

(52) U.S. Cl.
CPC ............ *G01N 35/00584* (2013.01); *G01N 1/44* (2013.01); *G01N 2035/00316* (2013.01); *G01N 2035/0406* (2013.01)
USPC ............ 422/68.1; 422/50; 422/400; 422/401; 422/402; 422/403; 422/404; 422/405; 422/408; 422/62; 422/63; 422/64; 422/65; 422/67; 422/73; 422/75; 422/82.05; 422/82.06; 422/82.07; 422/82.08; 422/82.09; 422/98; 422/500; 422/501; 422/504; 422/509; 422/510; 422/511; 422/512; 422/514; 422/515; 422/521; 422/526; 422/547; 422/549; 422/550; 422/554; 422/556; 422/557; 422/558; 422/559; 422/560; 422/561; 422/562; 422/939; 422/565; 422/566; 422/940

(58) Field of Classification Search
CPC ....................... G01N 1/44; G01N 2035/00316
USPC ........... 422/50, 400, 401, 402, 403, 404, 405, 422/408, 62, 63, 64, 65, 67, 68.1, 73, 75, 422/82.05, 82.07, 82.08, 82.09, 98, 500, 422/501, 504, 509, 510, 511, 512, 514, 515, 422/521, 526, 547, 549, 550, 554, 556, 557, 422/558, 559, 560, 561, 562, 565, 566, 939, 422/940; 436/43, 46, 47, 164, 165, 169, 436/170, 815, 817; 435/13, 283.1, 287.1, 435/287.7, 287.8, 287.9, 288.7
See application file for complete search history.

*Primary Examiner* — Dennis M White
(74) *Attorney, Agent, or Firm* — Sughrue Mion, PLLC

(57) ABSTRACT

A sample analysis apparatus configured to automatically press a start button upon installation of a sample tube is provided. The sample analysis apparatus includes: a body of the sample analysis apparatus; a door housing which may be provided in an opened state or a closed state, and configured to be coupled to the body of the sample analysis apparatus by a hinge; a tube accommodating unit included in the door housing and configured to accommodate the sample tube; a start button included in the body of the sample analysis apparatus and configured to start analysis of the sample; and an operating member positioned at a first position which is distant from the start button the sample tube is not installed in the tube accommodating unit, and a second position which is configured to operate the start button when a sample tube is installed and the door housing is closed.

18 Claims, 9 Drawing Sheets

(a)  (b)  (c)

SAMPLE ANALYSIS APPARATUS

CROSS-REFERENCE TO RELATED APPLICATION

This application claims priority from Korean Patent Application No. 10-2011-0077046, filed on Aug. 2, 2011 in the Korean Intellectual Property Office, the disclosure of which is incorporated herein by reference.

BACKGROUND

1. Field

Apparatuses consistent with exemplary embodiments relate to a sample analysis apparatus, more particularly, a sample analysis apparatus having an enhanced structure that enables the automatic pressing of a start button when a sample tube is inserted therein.

2. Description of the Related Art

A sample analysis apparatus may have a wide use for an analysis of a sample such as blood, urine, blood cells, etc.

Sample analysis apparatuses may be divided into types having a door and types not having a door. When the sample analysis apparatus has a door, a start button is manually pressed after moderately adjusting the height of a sample induction needle into a sample tube for a sample to be dipped, thereby starting a test along with the induction of the sample.

In a case where the sample analysis apparatus has a door, the start button may be pressed after the door is closed regardless of whether a sample tube is installed therein. Even after the installation of the sample tube, the start button still needs to be pressed by means of an additional action by the user.

Use of sample analysis apparatuses is in an increasing trend, and when the sample analysis apparatus has a door, if the test is started by the start button being pressed without the sample tube being installed, an error may occur in the induction sampling process. In addition, since the occurrence of the error is determined by referring to a result of the test after the test is completed, the error can be a significant waste of time. If is also a waste of time if the door needs to be closed and an additional action by a user is required to press the start button.

SUMMARY

Exemplary embodiments provide a sample analysis apparatus having a button that is pressed after a sample tube is installed within the sample analysis apparatus.

In accordance with an aspect of an exemplary embodiment, a sample analysis apparatus includes a body of the sample analysis apparatus within which analysis of a sample in a sample tube is conducted; a door housing configured to be coupled to the body of the sample analysis apparatus by a hinge; a tube accommodating unit included in the door housing and configured to accommodate the sample tube; a start button included in the body of the sample analysis apparatus and configured to start analysis of the sample; and an operating member positioned at a second position when a sample tube is installed in the tube accommodating unit, which is configured to operate the start button when the door housing is closed, and positioned at a first position which is distant from the start button when the sample tube is not installed in the tube accommodating unit.

The door housing may be rotatively opened toward the outside of the body of the sample analysis apparatus for insertion of the sample tube, and may be rotatively closed toward the inside of the sample analysis apparatus to begin analysis.

The start button may be positioned facing the tube accommodating unit.

The operating member may be coupled to one side of the door housing by a hinge, and may be a lever capable of rotating between the first position and the second position depending on whether the sample tube is installed in the tube accommodating unit.

The lever may include a lever operating unit extending toward the inside of the body of the sample analysis apparatus and capable of operating the start button, and a lever supporting unit coupled to the door housing by the hinge and configured to move the lever operating unit from the first position to the second position.

The tube accommodating unit, may include a groove disposed at a side facing the start button, through which the operating member may move.

The lever supporting unit may be coupled to a bottom surface of the tube accommodating unit, and the lever operating unit is moved from the first position to the second position as a result of being pressed by the sample tube installed in the tube accommodating unit.

The door housing may include a protrusion that extends from the bottom surface of the tube accommodating unit in order to prevent the lever from inclining when the sample tube is not installed.

The lever supporting unit may be coupled to an entrance side (i.e., a top surface) of the tube accommodating unit, and the lever supporting unit is capable of rotating while being pressed by the sample tube installed in the tube accommodating unit, thereby moving the lever operating unit from the first position to the second position.

The door housing may include a protrusion extending from the top surface of the tube accommodating unit in order to prevent the lever from inclining when the sample tube is not installed.

The sample analysis apparatus may further include a tube holder inserted into the tube accommodating unit, the tube holder being configured to accommodate the sample tube.

The tube holder may be composed of a body unit configured to accommodate the sample tube and a holder unit radially extending from the body unit to be supported by the tube accommodating unit.

The circumferential edge of the tube holder may protrude or extend radially with respect to an inner side thereof, in order to prevent the sample inside of the sample tube from spilling or overflowing down into the sample analysis apparatus.

A hinge coupling unit is configured to couple the lever and the door housing with a hinge, and may include an elastic member configured to change the lever from the first position to the second position.

The sample analysis apparatus may further include a light sensor having a light emitting unit provided at one side surface of the tube accommodating unit and configured to emit a light toward and through the sample in the sample tube for determining whether a sample is in the sample tube, and a light receiving unit provided at an opposing side surface of the tube accommodating unit and configured to receive light passing through the sample.

The light emitting unit and the light receiving unit may be disposed facing each other.

The sample analysis apparatus may further include a tube holder that is inserted into the tube accommodating unit and configured to support the sample tube, wherein the tube holder is composed of a transparent material.

The sample analysis apparatus may further include a weight sensor disposed at a lower side or a bottom surface of the tube accommodating unit for measuring the weight of a sample.

In accordance with another exemplary aspect, a sample analysis apparatus includes a body of the sample analysis apparatus within which analysis of a sample in a sample tube is conducted; a door housing configured to be coupled to the body of the sample analysis apparatus by a hinge; a tube accommodating unit included in the door housing and configured to accommodate the sample tube; and a start button located in the body of the sample analysis apparatus and positioned to be in contact with at least a portion of the sample tube that is inserted into the tube accommodating unit when the door housing is closed.

The start button may be mounted to a start button attachment unit, which is a portion of the body of the sample analysis apparatus that protrudes toward to the door housing so that the sample tube and the start button come into contact with each other when the door is closed.

The sample analysis apparatus may further include a tube holder that includes a body unit inserted in the tube accommodating unit and configured to accommodate the sample tube, and a holder unit radially extending from the body unit to be supported by the tube accommodating unit. The tube holder may further include a circumferential edge that protrudes toward an inner side of the holder unit.

In accordance with another exemplary aspect, a sample analysis apparatus includes a body of the sample analysis apparatus within which analysis of a sample in a sample tube is conducted; a door housing configured to be coupled to the body of the sample analysis apparatus by a hinge; a tube accommodating unit included in the door housing and configured to accommodate the sample tube; a weight sensor disposed at a lower side surface or a bottom surface of the tube accommodating unit, wherein the weight sensor encounters the sample tube and is configured to measure a weight of the sample tube; and a control unit electrically connected to the weight sensor and configured to determine whether the sample tube is installed based on the weight detected by the weight sensor, and when the sample tube is installed, initiate analysis of the sample.

The sample analysis apparatus may further include a tube holder that is composed of a body unit inserted into the tube accommodating unit and configured to accommodate the sample tube and a holder unit radially extending from the body unit to be supported by the tube accommodating unit, with a circumferential edge of the holder unit protruding toward an inner side of the holder unit.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
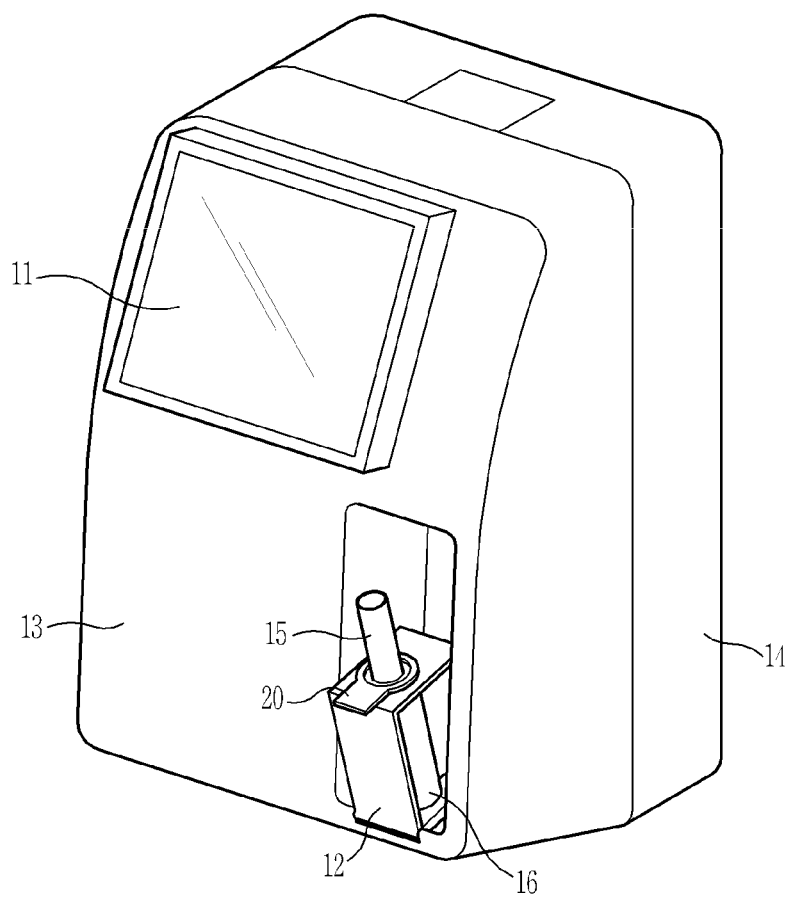
FIG. 1 is a view illustrating a structure of a sample analysis apparatus in accordance with an exemplary embodiment.

Reference will now be made in detail to exemplary embodiments, examples of which are illustrated in the accompanying drawings, wherein like reference numerals refer to like elements throughout.

FIG. 1 is a perspective view illustrating a structure of a sample analysis apparatus in accordance with an exemplary embodiment.

As illustrated in FIG. 1, a sample analysis apparatus 10 provides an input/output display unit 11, a door housing 12, a measuring analysis unit 13, and a control unit 14. The input/output display unit 11 is provided at the upper portion of the front surface of the body 19 of the sample analysis apparatus 10 and allows a user to input commands for performing sample analysis, and at the same time, displays analysis results in easy terms.

A tube accommodating unit 16 into which a sample tube 15 may be inserted, a start button 17 capable of starting a sample analysis, and a lever 30 classified as an operating member configured to start the start button 17 are provided at an inner side of the door housing 12. The control unit 14 electrically controls the operation of an analysis process of a sample through operation of the start button 17.

Figure 2:
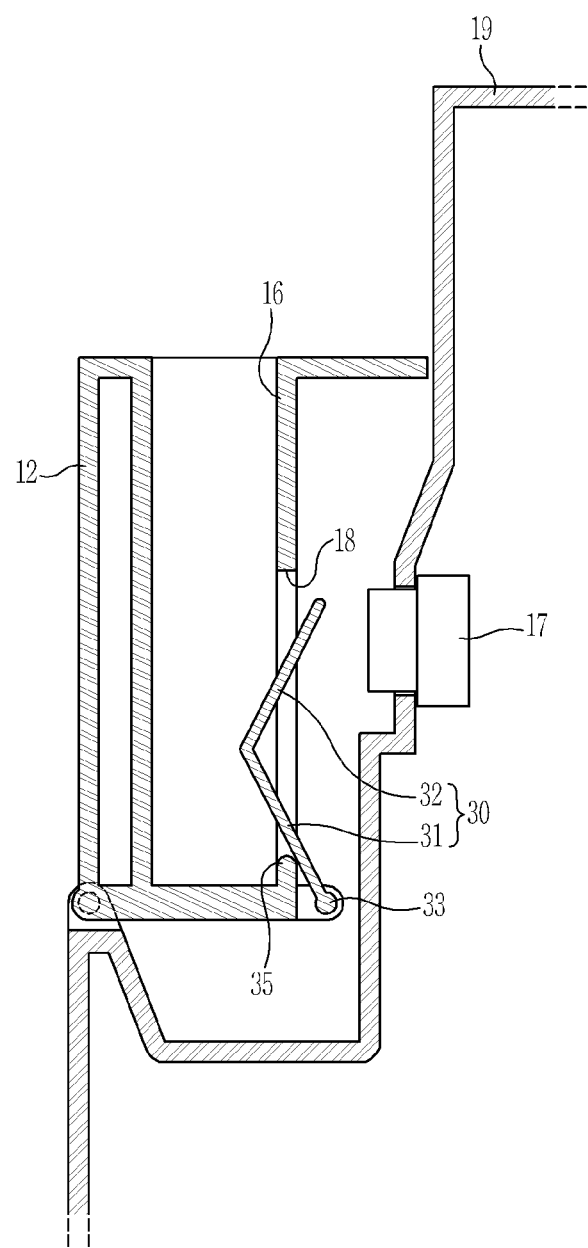
FIG. 2 is a sectional view of a sample analysis apparatus illustrating a state wherein a sample tube is not installed in the tube accommodating unit, in accordance with an exemplary embodiment.
Figure 3:
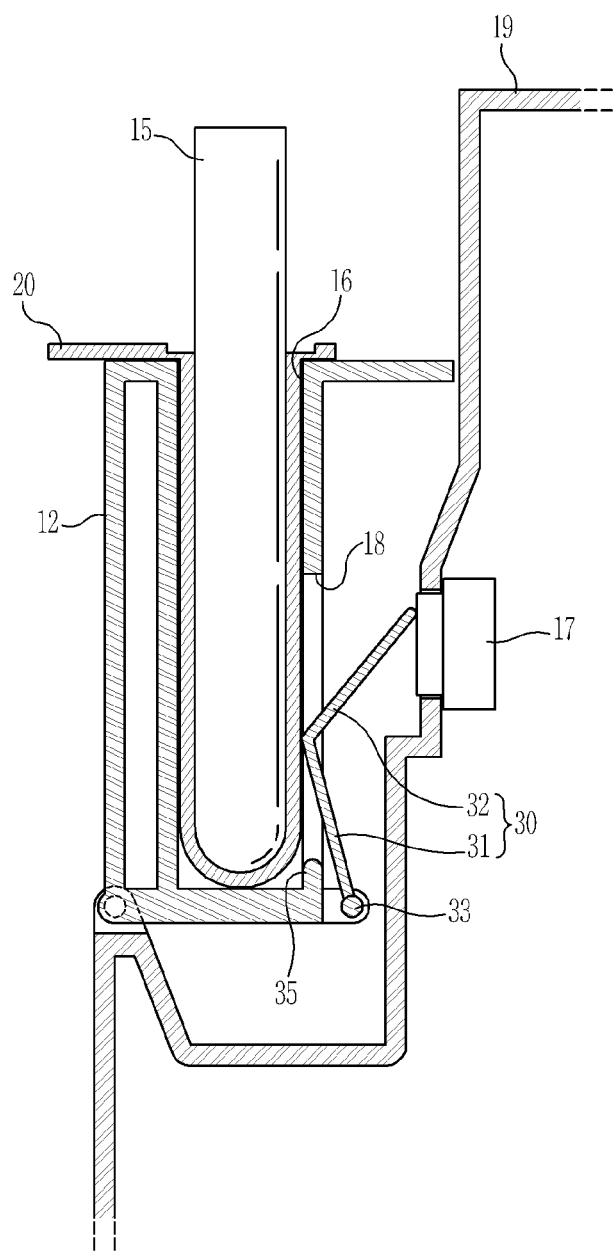
FIG. 3 is a sectional view of a sample analysis apparatus illustrating a state wherein a sample tube is installed in the tube accommodating unit, in accordance with an exemplary embodiment.

FIG. 2 is a sectional view illustrating a state wherein a sample tube is not installed in the sample accommodating unit of the sample analysis apparatus in accordance with an exemplary embodiment, and FIG. 3 is a sectional view illustrating a state wherein the sample tube is installed in the sample accommodating unit of the sample analysis apparatus in accordance with an exemplary embodiment.

As illustrated in FIGS. 2 and 3, the door housing 12 is coupled to the body 19 of the sample analysis apparatus 10 by a hinge. Therefore, by applying pressure to an outer side of the door housing 12, the door housing 12 is capable of rotating toward an outer side of the body 19 of the sample analysis apparatus 10. That is, when the door housing 12 is rotated toward the outer side of the body 19 of the sample analysis apparatus, it may be classified as being in an open state, and when the door housing 12 is rotated toward the inner side of the body 19 of the sample analysis apparatus, it may be classified as being in a closed state. When in the open state a sample tube 15 may be inserted into the tube accommodating unit 16 of the door housing 12. When pressure is applied to the door housing 12 after insertion of the sample tube 15, the door housing 12 is rotated toward the inner side of the body 19 of the sample analysis apparatus, and is changed to a closed state such that the sample analysis process may be started.

In addition, not only is the tube accommodating unit 16 capable of directly accommodating the sample tube 15, but it also is capable of accommodating the sample tube 15 supported by a tube holder 20. That is, the sample tube 15 may be inserted into a tube holder 20, and it is possible to insert the tube holder 20 into the tube accommodating unit 16.

The start button 17, which begins the sample analysis process is positioned at the inner side of the body 19 of the sample analysis apparatus. In an exemplary embodiment, the start button 17 may be positioned facing the tube accommodating unit 16. A lever 30 is coupled at the bottom surface of the tube accommodating unit 16 by a hinge. As such, when the sample tube 15 is inserted into the tube accommodating unit 16, the lever 30 moves toward the direction of the start button 17. Thus, when the door housing 12 is closed, the position of the lever 30 when the sample tube 15 is not installed is defined as a first position, and the position of the lever 30 when the sample tube 15 is installed is defined as a second position. When in the first position, the lever 30 is located near the start button 17, while maintaining a gap therebetween so as to avoid having the lever activate the start button 17. When the position of the lever 30 is changed to the second position, the lever 30 is able to operate the start button 17. Therefore, when the door housing 12 is rotated toward the inner side of the body 19 of the sample analysis apparatus (i.e., when the door housing 12 is closed) and the sample tube 15 has been inserted into the tube accommodating unit 16, the lever 30, being in the second position is capable of pressing the start button 17.

In order to facilitate a position change of the lever 30 from the first position to the second position, an elastic member 34 (see FIG. 4) may be provided at a hinge coupling unit 33 at the bottom surface of the tube accommodating unit 16. In addition, the tube accommodating unit 16 may be provided with a protrusion 35 that protrudes from the bottom surface of the accommodation unit 16. Such has an effect in stopping the lever 30 from inclining by no more than a few degrees when the sample tube 15 is not installed.

Figure 4:
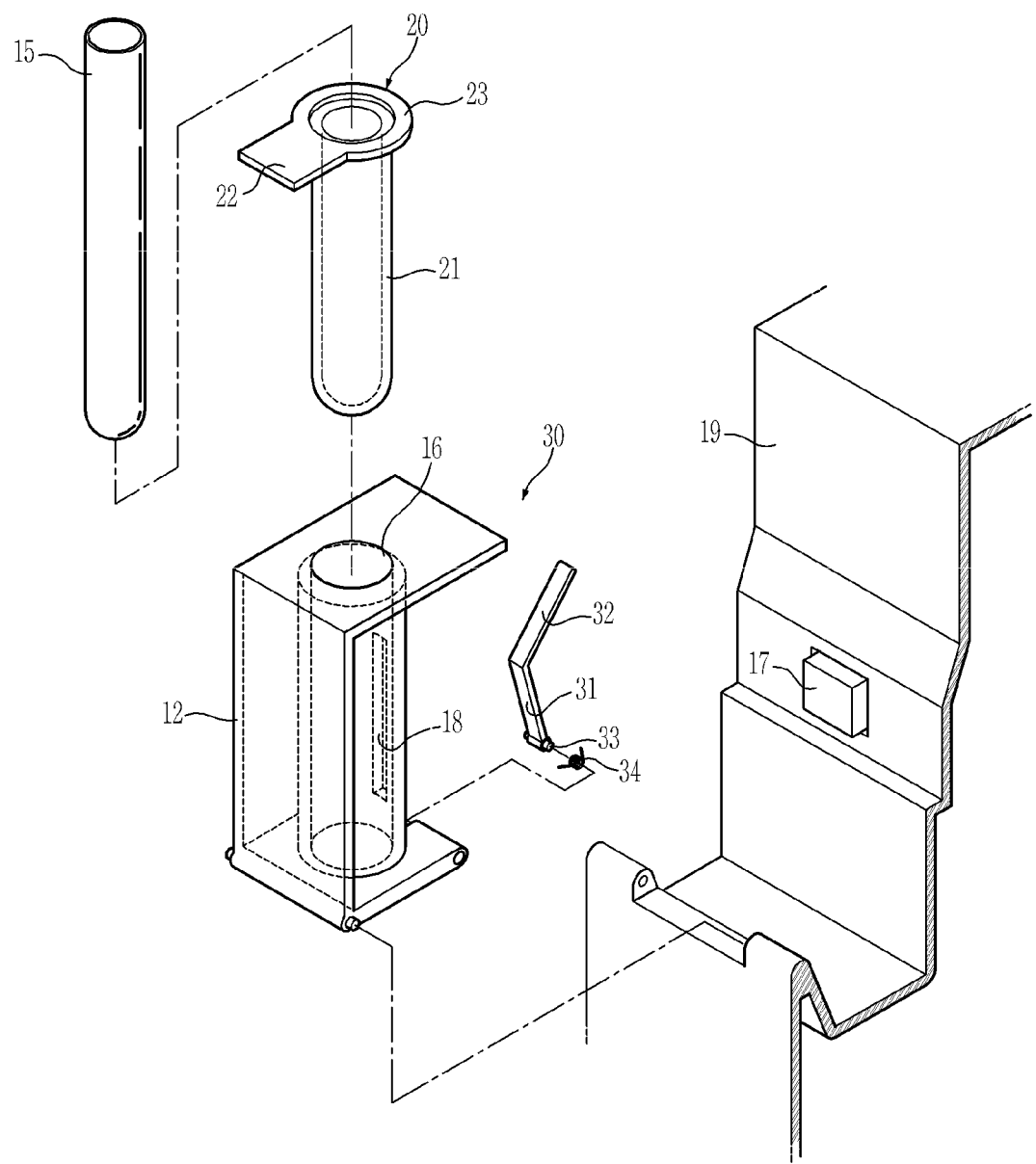
FIG. 4 is an exploded view illustrating a door housing, a body of the sample analysis apparatus, a sample tube, and a tube holder.

With continued reference to FIG. 4, a groove 18 may be disposed on the inner side of the tube accommodating unit 16 at which the start button 17 and the tube accommodating unit 16 face each other. Through the groove 18, the position of the lever 30 may be changed without frictional contact with the tube accommodating unit 16.

In an exemplary embodiment, the lever 30 is composed of a lever operating unit 32 extended toward the inner side of the body 19 of the sample analysis apparatus 10 for operating the start button 17, and a lever supporting unit 31 coupled to the door housing 12 by a hinge. The lever supporting unit 31 is configured to move the lever operating unit 32 from the first position to the second position, since the door housing 12 and the lever supporting unit 31 are coupled by a hinge. Thus, as the sample tube 15 is inserted into the tube accommodating unit 16, the lever operating unit 32 is pressed by the sample tube 15, and is then rotated toward the start button 17. When the door housing 12 is closed, the start button 17 is pressed by the lever operating unit 32.

A prescribed angle is formed between the lever supporting unit 31 and the lever operating unit 32, and such may be changed according to the position of the start button 17. However, in order to prevent friction between the body 19 of the sample analysis apparatus and the lever 30 from occurring by the movement of the lever 30, the angle is maintained at or greater than 90°.

In addition, a light sensor 40 (see FIG. 8) and a weight sensor 75 (see FIG. 9), which are capable of determining whether a sample exists may be included at a lower portion of the tube accommodating unit 16, as explained below.

FIG. 4 is an exploded view illustrating a door housing, a body of the sample analysis apparatus, the sample tube, and a tube holder.

The tube holder 20 is composed of a body unit 21 configured to accommodate the sample tube 15 and a holder unit 22 extended from the body unit 21 and supported by the tube accommodating unit 16. The body unit 21 includes a cylindrical tube that is able to accept an inserted sample tube 15. The body unit 21 may be manufactured in various ways and in various dimensions, depending on the length and the width of the sample tube 15. Therefore, by modifying the tube holder 20, a sample tube 15 of any size may be inserted into the accommodation unit 16, thereby enabling sample analysis.

Since the diameter of the holder unit 22 of the tube holder 20 is larger than that of the body unit 21, the holder unit 22 may be hung at the top of the tube accommodating unit 16 and/or the door housing 12. Thus, when the tube holder 20 is inserted into the tube accommodating unit 16, a portion of the holder unit 22 is protruded toward the outside of the sample analysis apparatus body 19, and therefore, the tube holder 20 and the sample tube 15 may be easily separated for individual insertion into and/or removal from the sample analysis apparatus 10.

In addition, the circumferential edge 23 of the holder unit 22 may extend outwardly with respect to the inside of the holder unit 22 to prevent spillage of the sample within the sample tube 15, and therefore, prevent overflow of the sample from affecting the sample analysis apparatus 10, as well as the analysis result.

The shape of the tube holder 20, as illustrated in the drawings, is not limited to a cylindrical shape, and may be rectangular or any other suitable shape. In addition, the tube holder 20 may be made from any suitable material, but is generally made of plastic, and when used in conjunction with the light sensor 40, may be a transparent material.

The door housing 12, including the tube accommodating unit 16, is coupled to the body 19 of the sample analysis apparatus at which the start button is located. In addition, the lever 30, composed of the lever supporting unit 31 and the lever operating unit 32, is coupled to the bottom surface of the tube accommodating unit 16 by a hinge, and the lever operating unit 32 is pressed by the inserted sample tube 15, thereby causing the lever 30 to rotate. The tube accommodating unit 16 may include a groove 18, in order for the movement of the lever 30 to be smooth. The tube holder 20 composed of the body unit 21 and the holder unit 22 may accommodate the sample tube 15 within the body unit 21. The tube holder 20 into which the sample tube 15 is inserted, is then inserted into the tube accommodating unit 16. When the door housing 12 is rotated toward the inner side of the body 19 of the sample analysis apparatus (i.e., is closed) by pressing the door housing 12, analysis of the sample begins as the lever 30 operates the start button 17.

Figure 5:
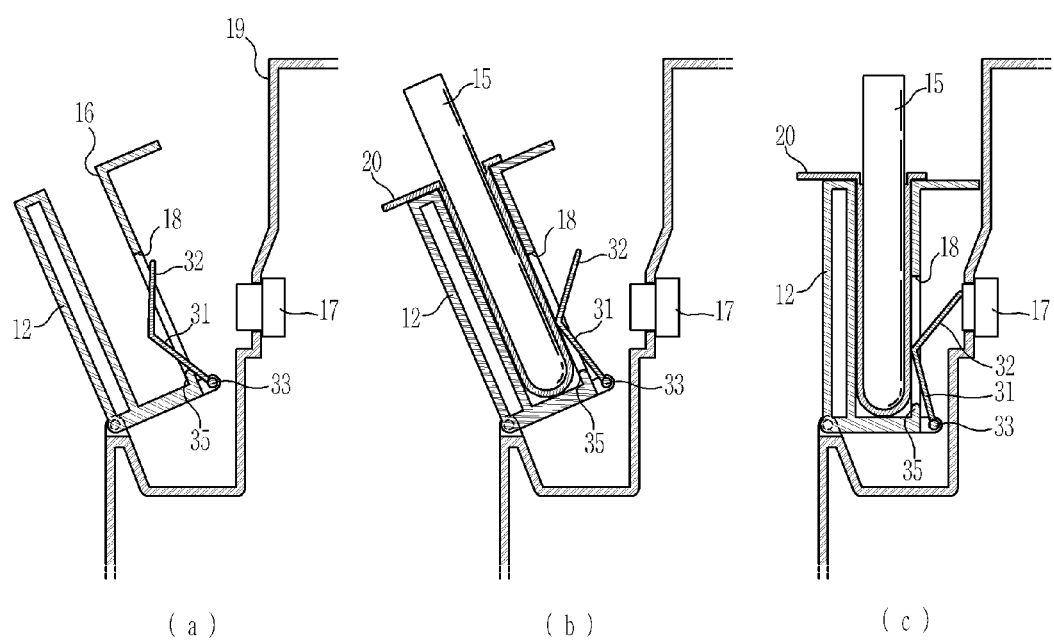
FIGS. 5A-5C are sectional views illustrating a process of inserting a sample tube into the sample analysis apparatus and a start button being pressed according to an exemplary embodiment.

FIGS. 5A to 5C are sectional views illustrating a process of installing the sample tube into the sample analysis apparatus, and a start button being pressed according to an exemplary embodiment.

FIG. 5A shows the sample analysis apparatus in a state prior to the sample tube 15 being installed into the tube accommodating unit 16 of the door housing 12, which is classified as being in the opened state. FIG. 5B is a drawing illustrating a sample tube 15 having been installed in the tube holder 20, which was then inserted into the tube accommodating unit 16 of the opened door housing 12. As a result of the installation of the sample tube 15, the lever 30 is moved toward the body 19 of the sample analysis apparatus. FIG. 5C shows the door housing 12 having been rotated toward the inner side of the sample analysis apparatus (i.e., the door housing is shown in a closed state). Because the lever 30 was moved into the second position by the insertion of the sample tube 15 in FIG. 5B, the lever 30 presses the start button 17 upon closing of the door housing 12.

Figure 6:
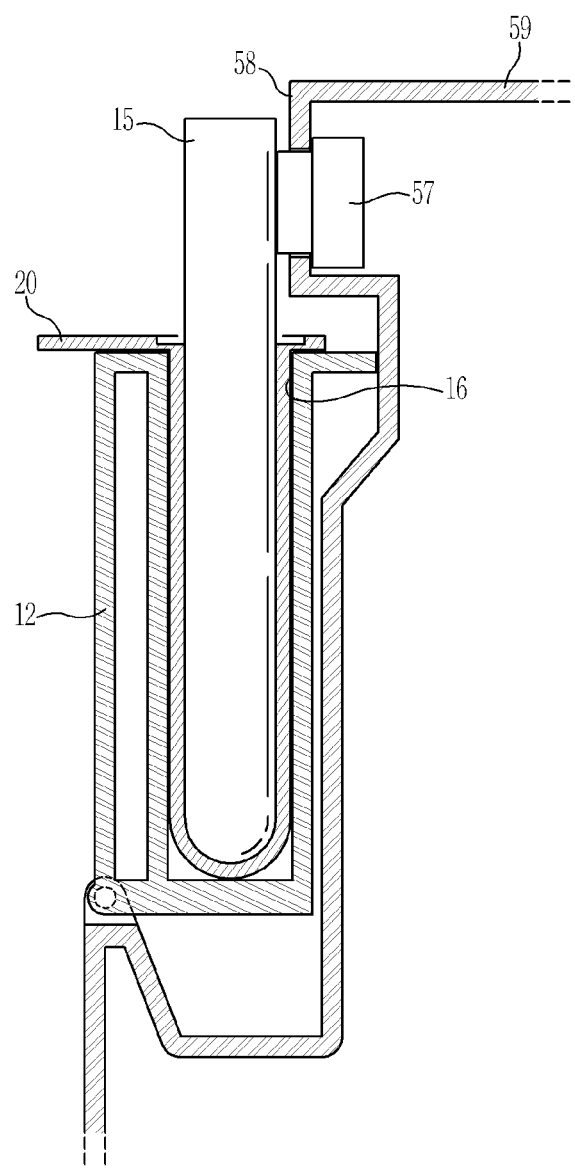
FIG. 6 is a sectional view of a sample analysis apparatus illustrating a state wherein a sample tube is installed in the tube accommodating unit of the sample analysis apparatus in accordance with another exemplary embodiment.

FIG. 6 is a sectional view illustrating a sample tube having been installed into the sample analysis apparatus in accordance with another exemplary embodiment.

As shown in FIG. 6, it is possible to operate a start button 57 by the insertion of the sample tube 15 even in the absence of an operating member, such as the lever 30. In this exemplary embodiment, the sample analysis apparatus includes a body 59 of the sample analysis apparatus within which analysis of the sample inside the sample tube 16 is conducted, and a door housing 12 coupled to the body 59 of the sample analysis apparatus by a hinge. The door housing 12 may be in an opened state (i.e., the door housing 12 is rotated toward the outer side of the body 59 of the sample analysis apparatus), or a closed state (i.e., the door housing 12 is rotated toward the inner side of the body 59 of the sample analysis apparatus).

As in the previous embodiment, the tube holder 20 and the sample tube 15 may be inserted into the tube accommodating unit 16 included in the door housing 12. The tube holder 20 is composed of the body unit 21 configured to accommodate the sample tube 15 and the holder unit 22 extending from the body unit 21 to be supported by the tube accommodating unit 16. The circumferential edge 23 of the holder unit 22 may extend with respect to the inner side of the holder unit 22 to prevent the sample from spilling or overflowing toward the body 59 of the sample analysis apparatus.

A start button 57 is disposed facing the sample tube 15 and protruding toward the upper surface of the tube accommodating unit 16 in order for the sample tube 15 and the start button 57 to make contact upon closing of the door housing 12. In addition, because the presence of a sample tube 15 is needed to operate the start button 57, a start button attachment unit 58 having the start button attached thereto may protrude in the direction of the sample tube with respect to the body 59 of the sample analysis apparatus.

Therefore, when the door housing 12 is closed after the sample tube 15 is inserted into the tube accommodating unit 16, the sample tube 15 presses the start button 17 equipped at the protruded portion 58 of the body 59 of the sample analysis apparatus to begin sample analysis.

It is advantageous that, without a separate operating member such as the lever 30, the sample tube 15 may be inserted at the tube accommodating unit 16 for the sample analysis to be started. In addition, one side surface of the tube accommodating unit 16 may include the light sensor 40 having a light emitting unit 41 and a light receiving unit 42, as discussed below.

Figure 7:
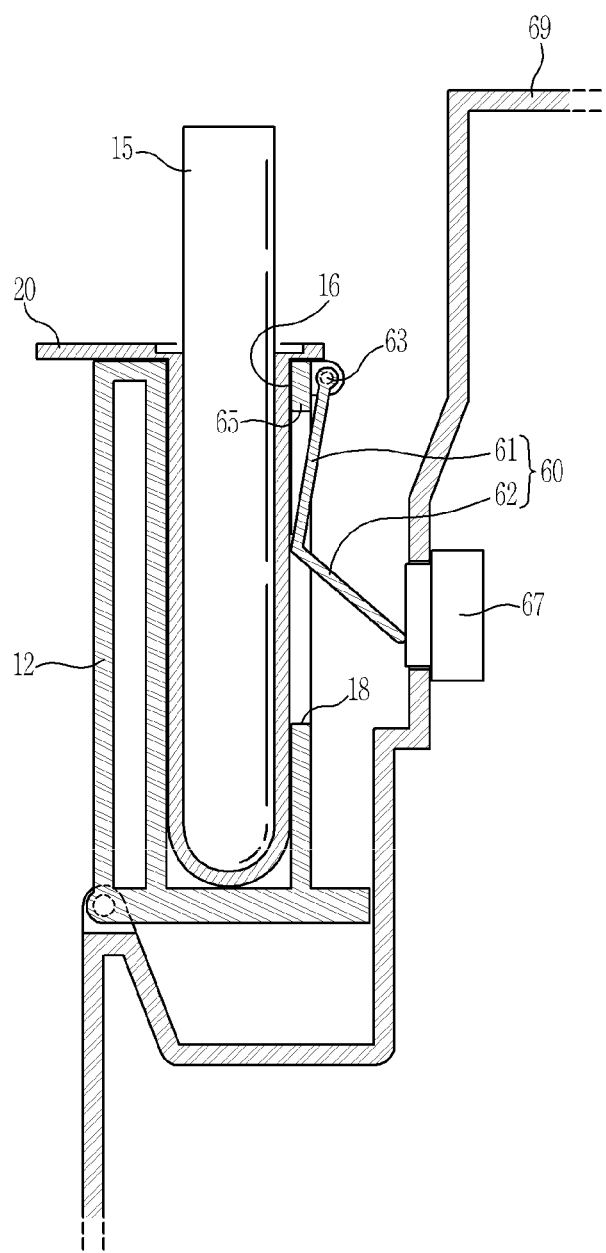
FIG. 7 is a sectional view of a sample analysis apparatus illustrating a state wherein a sample tube is installed in the tube accommodating unit of the sample analysis apparatus in accordance with another exemplary embodiment.

FIG. 7 is sectional a view illustrating a state of the sample tube installed at the sample analysis apparatus in accordance with another exemplary embodiment.

This embodiment differs from the embodiment illustrated in FIG. 3 with respect to the coupling position of the lever supporting unit 61 and the tube accommodating unit 16. According to this exemplary embodiment, the lever supporting unit 61 is coupled to the entrance side (i.e., top surface) of the tube accommodating unit 16. Accordingly, the lever supporting unit 61 is rotated by the insertion of the sample tube 15 into the tube accommodating unit 16 when the lever 60 moves from the first position to the second position. Accordingly, when the sample tube 15 is not installed, a protrusion 65, which is provided at the entrance side of the tube accommodating unit 16, prevents the lever 60 from inclining by no more than a certain degree.

In accordance with the exemplary embodiment illustrated in FIG. 7, when compared to the embodiment illustrated on FIG. 3, less friction occurs between the lever 60 and the sample tube 15, and/or the tube holder 20, thereby minimizing the burden on the lever 60. Accordingly, the probability of failure of the lever 60 is decreased, and the lifespan for the use of the sample analysis apparatus 10 is increased.

Figure 8:
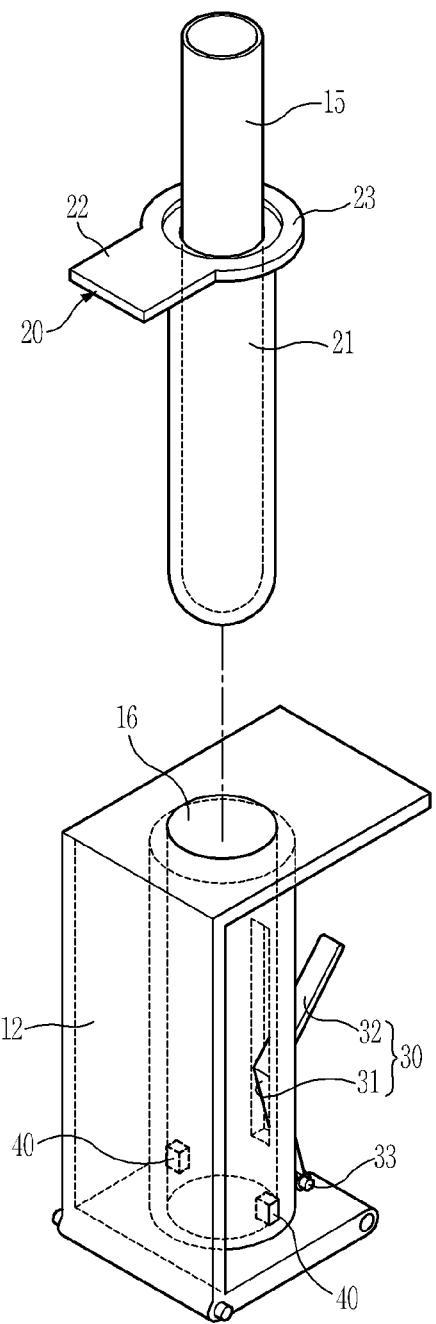
FIG. 8 is a perspective view illustrating the tube accommodating unit of the sample analysis apparatus having a light sensor according to the exemplary embodiment of FIG. 3.

FIG. 8 is a perspective view illustrating the sample analysis apparatus having a light sensor according to the exemplary embodiment shown in FIG. 3.

The light sensor 40 is configured to determine whether a sample is present in the sample tube 15, and may be disposed at one side surface of the lower portion of the tube accommodating unit 16. The light sensor 40 includes a light emitting unit 41 and a light receiving unit 42, both of which are positioned to face each other within the tube accommodating unit 16. When the light sensor 40 is being used, a tube holder 20 made of a transparent material is used. Thus, the light receiving unit 42 may be able to determine whether the sample exists in the sample tube 15 by detecting light emitted from the light emitting unit 42, which then collides with and passes through the sample.

Therefore, since the light sensor 40 may be used to determine whether a sample tube 15 is inserted into the sample accommodating unit 16, any errors that occur with respect to the sampling of the sample analysis may be reduced.

Figure 9:
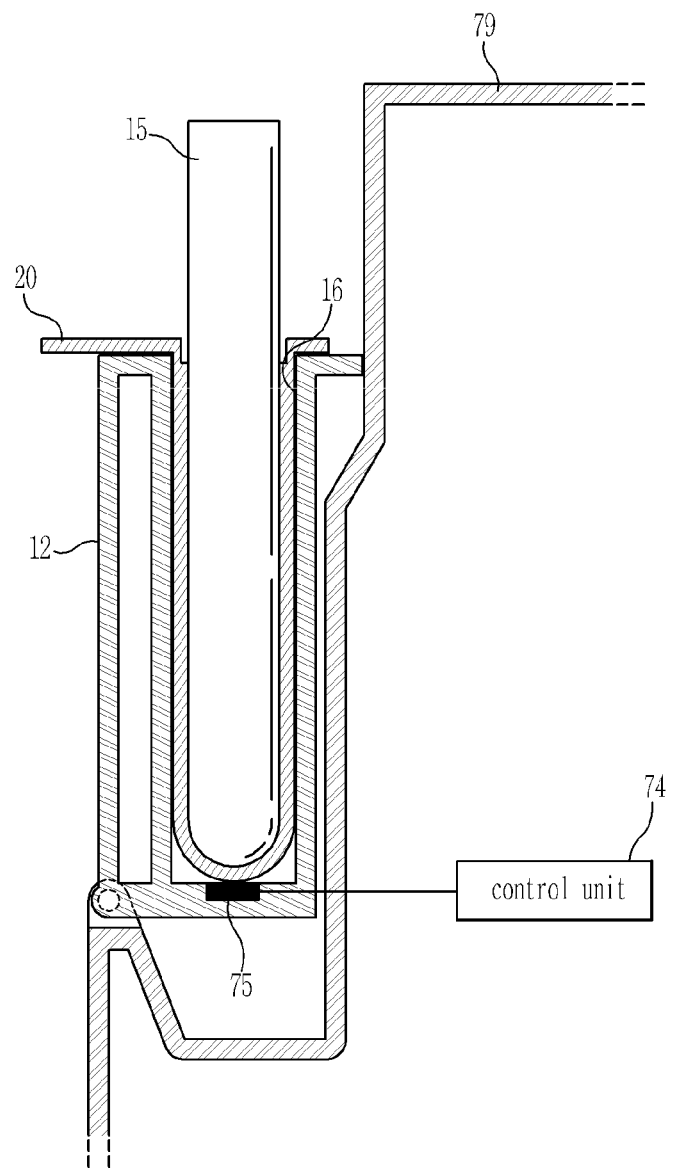
FIG. 9 is a sectional view of a sample analysis apparatus illustrating a state wherein a sample tube is installed in the tube accommodating unit of the sample analysis apparatus in accordance with another exemplary embodiment.

FIG. 9 is a sectional view illustrating a state of the sample tube installed in the sample analysis apparatus in accordance with another exemplary embodiment.

The sample analysis apparatus 10 includes a body 79 of the sample analysis apparatus within which sample analysis of the sample in the sample tube 15 is conducted, and a door housing 12 capable of being in a opened state and a closed state, thereby enabling insertion and/or removal of the sample tube 15 from the body 79 of the sample analysis apparatus. The door housing 12 includes the tube accommodating unit 16 configured to accommodate the sample tube 15.

As in the previous exemplary embodiments, not only the sample tube 15, but also the sample tube 15 accommodated in the tube holder 20 may be accommodated in the tube accommodating unit 16. The tube holder 20 is composed of the body unit 21 configured to accommodate the sample tube 15 and the holder unit 22 extended from the body unit 21 to be supported by the tube accommodating unit 16. In addition, the circumferential edge 23 of the holder unit 22 may extend with respect to the inner side of the holder unit 22 to prevent the sample from spilling or overflowing toward the body 79 of the sample analysis apparatus.

A weight sensor 75 may be provided at the lower portion of the tube accommodating unit 16. The weight sensor 75 is capable of measuring the weight of the sample tube 15 installed in the accommodating unit 16. In addition, since the weight sensor 75 is connected to the control unit 74, an electrical signal may be transmitted to the control unit 74 when the weight of the sample tube 15 is greater than the prescribed reference value. Therefore, by determining whether the sample tube 15 is installed using the weight sensor 75, it is possible to start the sample analysis.

Therefore, when the sample tube 15 having a sample therein is installed in the tube accommodating unit 16, the test may be started without a separate motion. This not only increases convenience from the perspective of the user, but also increases the credibility of the test result by preventing errors from the user from occurring by reducing actions required by the user with respect to the test, as well as reducing the test time.

Although exemplary embodiments have been shown and described, it should be appreciated by those skilled in the art that changes may be made in these embodiments without departing from the principles and spirit of the inventive concept, the scope of which is defined in the claims and their equivalents.

What is claimed is:

1. A sample analysis apparatus comprising:
a body within which analysis of a sample in a sample tube is conducted;
a door housing hingedly connected to the body;
a tube accommodating unit included in the door housing and configured to accommodate the sample tube;
a start button provided in the body and configured to begin analysis of the sample; and
an operating member positioned at a first position when the sample tube is not inserted into the tube accommodating unit, and positioned at a second position when the sample tube is inserted into the tube accommodating unit, wherein when the operating member is in the second position and the door housing is closed, the operating member actuates the start button.

2. The sample analysis apparatus of claim 1, wherein:
the door housing rotatively opens toward an outside of the body for insertion of the sample tube, and rotatively closes toward an inside of the body.

3. The sample analysis apparatus of claim 1, wherein:
the start button is positioned facing the tube accommodating unit.

4. The sample analysis apparatus of claim 1, wherein:
the operating member is hingedly coupled to a side of the door housing, and is a lever configured to rotate between the first position and the second position.

5. The sample analysis apparatus of claim 4, wherein:
the lever comprises a lever operating unit that extends toward an inside of the body, and a lever supporting unit hingedly coupled to the door housing and configured to move the lever operating unit from the first position to the second position.

6. The sample analysis apparatus of claim 1, wherein:
the tube accommodating unit comprises a groove disposed at a side facing the start button.

7. The sample analysis apparatus of claim 5, wherein:
the lever supporting unit is moved from the first position to the second position upon insertion of the sample tube into the tube accommodating unit.

8. The sample analysis apparatus of claim 7, wherein:
the door housing comprises a protrusion extending from a bottom surface of the tube accommodating unit in order to prevent the lever from inclining when the sample tube is not installed.

9. The sample analysis apparatus of claim 5, wherein:
the lever supporting unit is coupled to a top surface of the tube accommodating unit, and the lever supporting unit is moved from the first position to the second position upon insertion of the sample tube.

10. The sample analysis apparatus of claim 9, wherein:
the door housing comprises a protrusion extending from the top surface of the tube accommodating unit in order to prevent the lever from inclining when the sample tube is not installed.

11. The sample analysis apparatus of claim 1, further comprising:
a tube holder inserted into the tube accommodating unit, the tube holder being configured to accommodate the sample tube.

12. The sample analysis apparatus of claim 11, wherein:
the tube holder comprises a body unit configured to accommodate the sample tube and a holder unit extending from the body unit.

13. The sample analysis apparatus of claim 12, wherein:
a circumferential edge of the tube holder extends in a radial direction.

14. The sample analysis apparatus of claim 4, further comprising:
an elastic member disposed at the hinged coupling and configured to move the lever from the first position to the second position.

15. The sample analysis apparatus of claim 1, further comprising:
a light sensor including a light emitting unit that is provided at one side surface of the tube accommodating unit and configured to emit a light through the sample tube, and a light receiving unit that is provided at an opposing side surface of the tube accommodating unit and configured to receive light passing through the sample tube.

16. The sample analysis apparatus of claim 15, wherein:
the light emitting unit and the light receiving unit are disposed to face each other.

17. The sample analysis apparatus of claim 15, further comprising:
a tube holder configured to accommodate the sample tube, wherein the tube holder is made of a transparent material.

18. The sample analysis apparatus of claim 1, further comprising:
a weight sensor disposed at a lower side of the tube accommodating unit.

* * * * *